US009005609B2

(12) United States Patent
Pendharkar et al.

(10) Patent No.: US 9,005,609 B2
(45) Date of Patent: *Apr. 14, 2015

(54) HEMOSTATIC COMPOSITIONS CONTAINING STERILE THROMBIN

(75) Inventors: Sanyog M. Pendharkar, Pune (IN); Anne J. Gorman, Hightstown, NJ (US)

(73) Assignee: Ethicon, Inc., Somerville, NJ (US)

( * ) Notice: Subject to any disclaimer, the term of this patent is extended or adjusted under 35 U.S.C. 154(b) by 650 days.

This patent is subject to a terminal disclaimer.

(21) Appl. No.: 12/750,334

(22) Filed: Mar. 30, 2010

(65) Prior Publication Data

US 2010/0183582 A1    Jul. 22, 2010

Related U.S. Application Data

(63) Continuation of application No. 10/567,388, filed as application No. PCT/US2004/023765 on Jul. 23, 2004, now Pat. No. 7,718,412.

(60) Provisional application No. 60/493,116, filed on Aug. 7, 2003.

(51) Int. Cl.
| | |
|---|---|
| A61K 38/00 | (2006.01) |
| A61K 38/48 | (2006.01) |
| A61K 38/49 | (2006.01) |
| A61K 9/00 | (2006.01) |
| A61K 9/10 | (2006.01) |
| A61K 38/36 | (2006.01) |
| A61K 38/39 | (2006.01) |
| A61K 47/36 | (2006.01) |
| A61K 47/42 | (2006.01) |
| A61L 24/10 | (2006.01) |
| A61L 26/00 | (2006.01) |
| C12N 9/74 | (2006.01) |
| A61K 9/19 | (2006.01) |

(52) U.S. Cl.
CPC ............... *A61K 9/0019* (2013.01); *A61K 9/10* (2013.01); *A61K 9/19* (2013.01); *A61K 38/36* (2013.01); *A61K 38/363* (2013.01); *A61K 38/39* (2013.01); *A61K 38/4833* (2013.01); *A61K 47/36* (2013.01); *A61K 47/42* (2013.01); *A61L 24/104* (2013.01); *A61L 24/108* (2013.01); *A61L 26/0028* (2013.01); *A61L 26/0042* (2013.01); *A61L 26/0095* (2013.01); *A61L 2400/04* (2013.01); *C12N 9/6429* (2013.01); *C12Y 304/21005* (2013.01)

(58) Field of Classification Search
CPC ........... A61K 47/48215; A61K 31/728; A61K 31/79; A61K 38/40; A61K 2039/53; A61K 38/4813; A61K 39/00; A61K 38/4846; A61K 47/48746; A61K 47/48784; A61K 51/088; A61K 38/37; A61K 38/482; A61K 38/4833; A61K 38/4853; A61K 38/36; A61K 38/363; A61K 38/39; A61K 9/0019; A61K 2300/00; A61K 47/36; A61K 47/42; A61K 9/10; A61K 9/19; A61K 31/7151; A61K 9/12; A61K 38/00; A61K 47/10; A61K 47/186; A61K 2400/04

See application file for complete search history.

(56) References Cited

U.S. PATENT DOCUMENTS

| | | |
|---|---|---|
| 2,465,357 A | 3/1949 | Correll et al. |
| 2,507,244 A | 5/1950 | Correll |
| 2,558,395 A | 6/1951 | Studer |
| 2,899,362 A | 8/1959 | Sieger, Jr. et al. |
| 3,089,815 A | 5/1963 | Lieb et al. |
| 3,743,140 A | 7/1973 | Sauerbrey |
| 4,002,173 A | 1/1977 | Manning et al. |
| 4,006,220 A | 2/1977 | Gottlieb |
| 4,013,078 A | 3/1977 | Feild |
| 4,107,288 A | 8/1978 | Oppenheim et al. |
| 4,124,705 A | 11/1978 | Rothman et al. |
| 4,164,559 A | 8/1979 | Miyata et al. |
| 4,179,400 A | 12/1979 | Tsao et al. |
| 4,265,233 A | 5/1981 | Sugitachi et al. |
| 4,291,013 A | 9/1981 | Wahlig et al. |
| 4,292,972 A | 10/1981 | Pawelchak et al. |
| 4,298,598 A | 11/1981 | Schwarz et al. |
| 4,300,494 A | 11/1981 | Graiff et al. |
| 4,347,234 A | 8/1982 | Wahlig et al. |
| 4,362,567 A | 12/1982 | Schwarz et al. |
| 4,377,572 A | 3/1983 | Schwarz et al. |

(Continued)

FOREIGN PATENT DOCUMENTS

| | | |
|---|---|---|
| CA | 2495048 | 1/2005 |
| CN | 1270240 A | 10/2000 |

(Continued)

OTHER PUBLICATIONS

Wikipedia, the free encyclopedia, Hypertext address: en.wikipedia.org/wiki/Foaming_agent (Accessed on Apr. 13, 2007).
Wikipedia article (downloaded Nov. 9, 2007): 'Foam'; website: http://en.wikipedia.org/wiki/foam.
Merriam-Webster Entry (downloaded Nov. 9, 2007): "Foam":website: http//www.merriam-webster.com/dictionary/foam.
International Search Report dated Dec. 12, 2005 for corresponding Application No. PCT/US04/23799.
International Search Report dated Jul. 12, 2005 for corresponding Application No. PCT/US04/23765.
Sakurabayashi, "Clinical Evaluation of New Hemostatic Agent for Hemostasis from Biopsy Wounds in the Liver" Gastroenterological Endoscopy, vol. 30(1), (Oct. 1988) pp. 2256.

(Continued)

*Primary Examiner* — Debbie K Ware
(74) *Attorney, Agent, or Firm* — Roberts Mlotkowski Safran & Cole, PC

(57) ABSTRACT

The present invention includes sterilized hemostatic compositions that contain a continuous, biocompatible liquid phase having a solid phase of particles of a biocompatible polymer suitable for use in hemostasis and that is substantially insoluble in the liquid phase, and sterile thrombin, each of which is substantially homogenously dispersed throughout the continuous liquid phase, and methods for making such compositions.

6 Claims, No Drawings

(56) References Cited

U.S. PATENT DOCUMENTS

| | | | |
|---|---|---|---|
| 4,416,813 A | 11/1983 | Ikeda et al. | |
| 4,424,208 A | 1/1984 | Wallace et al. | |
| 4,453,939 A | 6/1984 | Zimmerman et al. | |
| 4,482,386 A | 11/1984 | Wittwer et al. | |
| 4,515,637 A | 5/1985 | Cioca | |
| 4,536,387 A | 8/1985 | Sakamoto et al. | |
| 4,540,410 A | 9/1985 | Wood et al. | |
| 4,543,332 A | 9/1985 | Jao et al. | |
| 4,554,156 A | 11/1985 | Fischer et al. | |
| 4,600,574 A | 7/1986 | Lindner et al. | |
| 4,640,834 A | 2/1987 | Eibl et al. | |
| 4,655,211 A | 4/1987 | Sakamoto et al. | |
| 4,696,812 A | 9/1987 | Silbering et al. | |
| 4,743,229 A | 5/1988 | Chu | |
| 4,746,514 A | 5/1988 | Warne | |
| 4,749,689 A | 6/1988 | Miyata et al. | |
| 4,803,075 A | 2/1989 | Wallace et al. | |
| 4,818,517 A | 4/1989 | Kwee et al. | |
| 4,832,686 A | 5/1989 | Anderson | |
| 4,837,285 A | 6/1989 | Berg et al. | |
| 4,885,161 A | 12/1989 | Cornell | |
| 4,891,359 A | 1/1990 | Saferstein et al. | |
| 4,925,677 A | 5/1990 | Feijen | |
| 4,936,835 A | 6/1990 | Haaga | |
| 4,946,870 A | 8/1990 | Partain, III et al. | |
| 4,965,203 A | 10/1990 | Silbering et al. | |
| 5,007,916 A | 4/1991 | Linsky et al. | |
| 5,017,229 A | 5/1991 | Burns et al. | |
| 5,023,082 A | 6/1991 | Friedman et al. | |
| 5,041,292 A | 8/1991 | Feijen | |
| 5,061,274 A | 10/1991 | Kensey | |
| 5,061,492 A | 10/1991 | Okada et al. | |
| 5,080,893 A | 1/1992 | Goldberg et al. | |
| 5,108,421 A | 4/1992 | Fowler | |
| 5,126,141 A | 6/1992 | Henry | |
| 5,129,882 A | 7/1992 | Weldon et al. | |
| 5,134,229 A | 7/1992 | Saferstein et al. | |
| 5,135,751 A | 8/1992 | Henry et al. | |
| 5,135,755 A | 8/1992 | Czech et al. | |
| 5,140,016 A | 8/1992 | Goldberg et al. | |
| 5,143,838 A | 9/1992 | Kraus et al. | |
| 5,149,540 A | 9/1992 | Kunihiro et al. | |
| 5,162,430 A | 11/1992 | Rhee et al. | |
| 5,165,938 A | 11/1992 | Knighton | |
| 5,178,883 A | 1/1993 | Knighton | |
| 5,192,300 A | 3/1993 | Fowler | |
| 5,196,185 A | 3/1993 | Silver et al. | |
| 5,204,382 A | 4/1993 | Wallace et al. | |
| 5,209,776 A | 5/1993 | Bass et al. | |
| 5,219,328 A | 6/1993 | Morse et al. | |
| 5,275,616 A | 1/1994 | Fowler | |
| 5,281,528 A | 1/1994 | Boctor et al. | |
| 5,292,632 A | 3/1994 | Maskasky et al. | |
| 5,300,494 A | 4/1994 | Brode, II et al. | |
| 5,304,377 A | 4/1994 | Yamada et al. | |
| 5,306,501 A | 4/1994 | Viegas et al. | |
| 5,324,775 A | 6/1994 | Rhee et al. | |
| 5,328,955 A | 7/1994 | Rhee et al. | |
| 5,330,446 A | 7/1994 | Weldon et al. | |
| 5,350,573 A | 9/1994 | Goldberg et al. | |
| 5,352,715 A | 10/1994 | Wallace et al. | |
| 5,356,614 A | 10/1994 | Sharma | |
| 5,384,333 A | 1/1995 | Davis et al. | |
| 5,385,606 A | 1/1995 | Kowanko | |
| 5,397,704 A | 3/1995 | Boctor et al. | |
| 5,399,361 A | 3/1995 | Song et al. | |
| 5,418,222 A | 5/1995 | Song et al. | |
| 5,428,022 A | 6/1995 | Palefsky et al. | |
| 5,428,024 A | 6/1995 | Chu et al. | |
| 5,437,672 A | 8/1995 | Allyne | |
| 5,447,966 A | 9/1995 | Hermes et al. | |
| 5,478,352 A | 12/1995 | Fowler | |
| 5,507,744 A | 4/1996 | Tay et al. | |
| 5,510,418 A | 4/1996 | Rhee et al. | |
| 5,512,301 A | 4/1996 | Song et al. | |
| 5,514,379 A | 5/1996 | Weissleder et al. | |
| 5,516,532 A | 5/1996 | Atala et al. | |
| 5,520,925 A | 5/1996 | Maser | |
| 5,531,759 A | 7/1996 | Kensey et al. | |
| 5,540,715 A | 7/1996 | Katsaros et al. | |
| 5,580,923 A | 12/1996 | Yeung et al. | |
| 5,595,735 A | 1/1997 | Saferstein et al. | |
| 5,599,735 A | 2/1997 | Moslehi | |
| 5,614,587 A | 3/1997 | Rhee et al. | |
| 5,618,551 A | 4/1997 | Tardy et al. | |
| 5,643,596 A | 7/1997 | Pruss et al. | |
| 5,648,506 A | 7/1997 | Desai et al. | |
| 5,658,592 A | 8/1997 | Tanihara et al. | |
| 5,667,839 A | 9/1997 | Berg | |
| 5,672,336 A | 9/1997 | Sharma | |
| 5,674,275 A | 10/1997 | Tang et al. | |
| 5,677,284 A | 10/1997 | Li | |
| 5,690,675 A | 11/1997 | Sawyer et al. | |
| 5,698,213 A | 12/1997 | Jamiolkowski et al. | |
| 5,714,370 A | 2/1998 | Eibl et al. | |
| 5,733,572 A | 3/1998 | Unger et al. | |
| 5,752,974 A | 5/1998 | Rhee et al. | |
| 5,770,229 A | 6/1998 | Tanihara et al. | |
| 5,853,749 A | 12/1998 | Hobbs | |
| 5,856,356 A | 1/1999 | Tsouderos et al. | |
| 5,861,043 A | 1/1999 | Carn | |
| 5,874,500 A | 2/1999 | Rhee et al. | |
| 5,902,832 A | 5/1999 | Van Bladel et al. | |
| 5,908,054 A | 6/1999 | Safabash et al. | |
| 5,931,165 A | 8/1999 | Reich et al. | |
| 5,959,735 A | 9/1999 | Maris et al. | |
| 5,997,895 A | 12/1999 | Narotam et al. | |
| 6,045,570 A | 4/2000 | Epstein et al. | |
| 6,063,061 A | 5/2000 | Wallace et al. | |
| 6,066,325 A | 5/2000 | Wallace et al. | |
| 6,096,309 A | 8/2000 | Prior et al. | |
| 6,110,484 A | 8/2000 | Sierra | |
| 6,120,751 A | 9/2000 | Unger | |
| 6,129,761 A | 10/2000 | Hubbell | |
| 6,132,759 A | 10/2000 | Schacht et al. | |
| 6,166,130 A | 12/2000 | Rhee et al. | |
| 6,179,872 B1 | 1/2001 | Bell et al. | |
| 6,277,394 B1 | 8/2001 | Sierra | |
| 6,312,474 B1 | 11/2001 | Francis et al. | |
| 6,312,725 B1 | 11/2001 | Wallace et al. | |
| 6,328,229 B1 | 12/2001 | Duronio et al. | |
| 6,432,415 B1 | 8/2002 | Osborne et al. | |
| 6,458,386 B1 | 10/2002 | Schacht et al. | |
| 6,458,889 B1 | 10/2002 | Trollsas | |
| 6,566,345 B2 | 5/2003 | Miller et al. | |
| 6,605,066 B1 | 8/2003 | Gravagna et al. | |
| 6,624,245 B2 | 9/2003 | Wallace et al. | |
| 6,706,690 B2 | 3/2004 | Reich et al. | |
| 6,706,962 B2 | 3/2004 | Nelles et al. | |
| 6,831,058 B1 | 12/2004 | Ikada et al. | |
| 6,869,938 B1 | 3/2005 | Schwartz et al. | |
| 6,887,974 B2 | 5/2005 | Pathak | |
| 7,109,163 B2 | 9/2006 | Pendharkar et al. | |
| 7,320,962 B2 | 1/2008 | Reich et al. | |
| 7,351,561 B2 | 4/2008 | Metzner et al. | |
| 7,435,425 B2 | 10/2008 | Qian et al. | |
| 7,547,446 B2 | 6/2009 | Qian et al. | |
| 7,718,412 B2 * | 5/2010 | Pendharkar et al. | 435/214 |
| 7,833,965 B2 * | 11/2010 | Pendharkar et al. | 514/13.6 |
| 7,871,637 B2 | 1/2011 | Qian et al. | |
| 8,303,981 B2 | 11/2012 | Wallace et al. | |
| 8,357,378 B2 | 1/2013 | Wallace et al. | |
| 2002/0042378 A1 | 4/2002 | Reich et al. | |
| 2002/0114775 A1 | 8/2002 | Pathak | |
| 2002/0193448 A1 | 12/2002 | Wallace et al. | |
| 2003/0028140 A1 | 2/2003 | Greff | |
| 2003/0064109 A1 | 4/2003 | Qian et al. | |
| 2003/0077272 A1 | 4/2003 | Pathak | |
| 2003/0129183 A1 | 7/2003 | Spillert et al. | |
| 2005/0037088 A1 | 2/2005 | Pendharkar et al. | |
| 2006/0127488 A1 | 6/2006 | Pendharkar et al. | |
| 2006/0147492 A1 | 7/2006 | Hunter et al. | |
| 2006/0167561 A1 | 7/2006 | Odar et al. | |
| 2008/0085316 A1 | 4/2008 | Qian et al. | |

(56) References Cited

U.S. PATENT DOCUMENTS

| | | |
|---|---|---|
| 2008/0091277 A1 | 4/2008 | Deusch et al. |
| 2008/0286376 A1 | 11/2008 | Qian et al. |
| 2009/0142396 A1 | 6/2009 | Odar et al. |
| 2010/0028309 A1 | 2/2010 | Odar et al. |
| 2010/0292717 A1 | 11/2010 | Petter-Puchner et al. |
| 2010/0318048 A1 | 12/2010 | Hoeffinghoff et al. |

FOREIGN PATENT DOCUMENTS

| | | |
|---|---|---|
| EP | 0132983 A1 | 7/1984 |
| EP | 0282316 A2 | 9/1988 |
| EP | 0341007 B1 | 11/1989 |
| EP | 0132983 B2 | 6/1991 |
| EP | 0172710 B1 | 3/1992 |
| EP | 0493387 B1 | 10/1993 |
| EP | 0376931 B1 | 6/1994 |
| EP | 0612252 B1 | 5/1999 |
| EP | 1084720 A1 | 3/2001 |
| EP | 1283063 A1 | 2/2003 |
| EP | 0 740 528 B1 | 3/2003 |
| EP | 0 927 253 B1 | 4/2003 |
| EP | 0927053 B1 | 4/2003 |
| EP | 0891193 B1 | 8/2003 |
| EP | 1484070 A2 | 12/2004 |
| EP | 1 559 438 A1 | 8/2005 |
| EP | 1414370 B1 | 4/2007 |
| GB | 1 018 647 | 1/1966 |
| JP | 51125156 B2 | 11/1976 |
| JP | 59113889 A | 6/1984 |
| JP | 62228009 | 10/1987 |
| JP | 2-218616 | 8/1990 |
| JP | 05308969 A | 11/1993 |
| JP | 6254148 B2 | 9/1994 |
| JP | 08024325 A | 1/1996 |
| JP | 9504719 A | 5/1997 |
| JP | 2000-229882 A | 8/2000 |
| JP | 2001-261574 A | 9/2001 |
| JP | 2002-104996 A | 4/2002 |
| JP | 2003-501215 | 1/2003 |
| JP | 07090241 A | 4/2007 |
| KR | 910007847 B1 | 10/1991 |
| WO | 8600912 A1 | 2/1986 |
| WO | 2006118460 A1 | 11/1989 |
| WO | 9221354 A1 | 12/1992 |
| WO | 9222252 A1 | 12/1992 |
| WO | 9427630 A1 | 8/1994 |
| WO | 94/23788 | 10/1994 |
| WO | 9512371 A1 | 5/1995 |
| WO | 9515747 A1 | 6/1995 |
| WO | 9604025 A1 | 2/1996 |
| WO | 9606883 A1 | 3/1996 |
| WO | 9610374 A1 | 4/1996 |
| WO | 9610428 A1 | 4/1996 |
| WO | 9614368 A1 | 5/1996 |
| WO | 9639159 A1 | 12/1996 |
| WO | 9737694 A1 | 10/1997 |
| WO | 98/08550 | 3/1998 |
| WO | 9913902 A1 | 3/1999 |
| WO | 9938606 A1 | 8/1999 |
| WO | 00/33894 | 6/2000 |
| WO | 00/76533 | 12/2000 |
| WO | 01/28603 | 4/2001 |
| WO | 01/82937 A1 | 11/2001 |
| WO | 01/97826 | 12/2001 |
| WO | 01/97873 | 12/2001 |
| WO | 0222184 A2 | 3/2002 |
| WO | 02/072128 | 9/2002 |
| WO | 02070594 A2 | 9/2002 |
| WO | 03/007845 | 1/2003 |
| WO | 03/055531 | 7/2003 |
| WO | 2004108179 A1 | 12/2004 |
| WO | 2005/016256 | 2/2005 |
| WO | 2005/016257 | 2/2005 |
| WO | 2005072700 A2 | 8/2005 |
| WO | 2006031358 A2 | 3/2006 |
| WO | 2007001926 A2 | 1/2007 |
| WO | 2007137839 A2 | 12/2007 |
| WO | 2007137839 A3 | 12/2007 |
| WO | 2008016983 A2 | 2/2008 |

OTHER PUBLICATIONS

Supplementary European Search Report dated Aug. 21, 2009 for corresponding application No. EP04779021.
Supplementary European Search Report dated Sep. 8, 2009 for corresponding application No. EP04757245.
U.S. Appl. No. 60/493,116, filed Aug. 7, 2003.
U.S. Appl. No. 10/896,647, filed Jul. 22, 2004.
International Application No. PCT/US04/23765 filed Jul. 23, 2004.
International Application No. PCT/US04/23799 filed Jul. 23, 2004.
U.S. Appl. No. 10/768,335, filed Jan. 30, 2004.
U.S. Appl. No. 10/896,454, filed Jul. 21, 2004.
U.S. Appl. No. 11/264,584, filed Nov. 1, 2005.
U.S. Appl. No. 10/567,388, filed Feb. 7, 2006.
U.S. Appl. No. 11/348,860, filed Feb. 7, 2006.
U.S. Appl. No. 12/750,334, filed Mar. 30, 2010.
U.S. Appl. No. 12/902,017, filed Oct. 11, 2010.
http://www.mathopenref.com/angle.html (accessed Oct. 8, 2008).
Taheri, "Technique for passing shunt tubbing subcutaneously", J. Neurosurg., 1971.
Wilkinson, et al., "Gelfoam paste in experimental laminectomy and cranial trephination", J. Neurosurg., 1981, vol. 54, pp. 664-667.
Gurney, et al., "Bioadhesive intraoral release systems: design, testing and analysis", Biomaterials, 1984, vol. 5, pp. 336-340.
Renkens, et al., "A Multicenter, Prospective, Randomized Trial Evaluating a New Hemostatic Agent for Spinal Surgery", Spine, 2001, vol. 26, No. 15, pp. 1645-1650.
Gall, et al., "Controll of Bleeding in Endoscopic Sinus Surgery: Use of a Novel Gelatin-Based Hemostatic Agent", The Journal of Otolaryngology, 2002, vol. 31, pp. 271-273.
Oz, et al., "Floseal Matrix: New Generation Topical Hemostatic Sealant", J. Card. Surg., 2003, vol. 18, pp. 486-493.
Ofner, III, et al., "Chemical and Swelling Evaluations of Amino Group Crosslinking in Gelatin and Modified Gelatin Matrices", Pharmaceutical Research, 1996, vol. 13, pp. 1821-1827.
Vandelli, et al., "The effect of the cross-linking time period upon the drug release and the dynamic swelling of gelatin microspheres", Pharmazie, 1991, vol. 46, pp. 866-869.
Duchene, et al., Drug Development and Industrial Pharmacy, 1988, vol. 14, No. 1, pp. 283-318.
Peppas, "Hydrogels and Drug Delivery", N. Curr. Opinion Coll. Interac. Sci., 1997, pp. 531-537.
Peppas, et al., "Preparation, structure and diffusional behavior of hydrogels in controlled release", Advanced Drug Delivery Reviews, 1993, vol. 11, pp. 1-35.
Miller, et al., "Diffusional Effects During Albumin Adsorption on Highly Swollen Poly (Vinyl Alcohol) Hydrogels", Eur. Polym. J., 1988, vol. 24, No. 7, pp. 611-615.
Brannon-Peppas, et al., "Absorbent Polymer Technology", Elsevier, 1990, pp. 67-102.
Peppas, et al., "Hydrogels in Medicine and Pharmacy", Peppas ed., vol. 1, Ch. 1, pp. 1-25, 1986.
Peppas, et al., "Hydrogels in Medicine and Pharmacy", Peppas ed., vol. 1, ch. 2, pp. 27-56, 1986.
Peppas, et al., "Hydrogels in Medicine and Pharmacy", Peppas ed., vol. 1, ch. 3, pp. 57-83, 1986.
Ratner, "Hydrogels in Medicine and Pharmacy", Peppas, ed., vol. 1, ch. 4, pp. 85-94, 1986.
Peppas, "Hydrogels in Medicine and Pharmacy", Peppas, ed., vol. 2, ch. 1, pp. 1-48, 1987.
Peppas, et al., "Hydrogels in Medicine and Pharmacy", Peppas, ed., vol. 2, ch. 2, pp. 49-64, 1987.
Kost, et al., "Hydrogels in Medicine and Pharmacy", Peppas, ed., vol. 3, ch. 5, pp. 95-108, 1987.
Peppas, et al., "Hydrogels in Medicine and Pharmacy", Peppas, ed., vol. 3, ch. 6, pp. 109-136, 1987.
Peppas, "Hydrogels in Medicine and Pharmacy", Peppas, ed., vol. 3, ch. 9, pp. 117-186, 1987.

(56) References Cited

OTHER PUBLICATIONS

Baxter, Instructions for Use, GentaFleece, Collagen Fleece, 2002, pp. 1-4.

Narotam, et al., "A clinicopathological study of collagen sponge as a dural graft in neurosurgery", J. Neurosurg., 1995, pp. 406-412.

Narotam, et al., "Experimental evaluation of collagen sponge as a dural graft", British J. of Neurosurg., 1993, vol. 7, pp. 635-641.

Nimni, et al., "Chemically modified collagen: A natural biomaterial for tissue replacement", Journal of Biomedical Materials Research, 1987, vol. 21, pp. 741-771.

Nimni, et al., "The Cross-Linking and Structure Modification of the Collagen Matrix in the Design of Cardiovascular Prosthesis", Journal of Cardiac Surgery, 1988, vol. 3, No. 4, pp. 523-533.

O'Neill, et al., "Use of porcine dermis as a dural substitute in 72 patients", J. Neurosurg., 1984, vol. 61, pp. 351-354.

Palm, et al., "Dural Closure with Nonpenetrating Clips Prevents Meningoneural Adhesions: An Experimental Study in Dogs", Neurosurgery, 1999, vol. 45, No. 4, pp. 875-882.

Parizek, et al., "Detailed Evaluation of 2959 Allogeneic and Xenogeneic Dense Connective Tissue Grafts (Fasia Lata, Pericardium, and Dura Mater) Used in the Course of 20 Years for Duraplasty in Neurosurgery", Acta Neurochirugica, 1997, vol. 139, pp. 827-838.

Park, et al., "Prevention of Arachnoiditis and Postoperative Tethering of the Spinal Cord wit Gore-Tex Surgical Membrane: An Experimental Study with Rats", Neurosurgery, 1998, vol. 42, No. 4, pp. 813-824.

Pietrucha, "New collagen implant as dural substitute", Biomaterials, 1991.

Pitt, et al., "Controlled Release of Bioactive Materials", Academic Press, 1980, pp. 20-43.

Porchet, "Inhibition of epidural fibrosis with ADCON-L: Effect on clinical outcome one year following re-operation for recurrent lumbar radiculopathy", Neurological Research, 1999, vol. 21, pp. 551-560.

Raul, et al., "Utilisation Du Polyester Urethane (Neuro-Patch) Comme Substitute Dural", Neurochirugie, 2003 (English Abstract).

Reddy, et al., "A Clinical Study of a Fibrinogen-Based Collagen Fleece for Dural Repair in Neurosurgery", Acta Neurochirurgica, 2002, pp. 265-269.

Riley, et al., "Percutaneous Liver Biopsy with Plugging of Needle Track: A safe Method for Use in Patients with Impaired Coagulation", Lancet, 1984, pp. 436.

Rosenblatt, et al., "Effect of electrostatic forces on the dynamic rheological properties of injectable collagen biomaterials", Biomaterials, 1992, vol. 13, No. 12, pp. 878-886.

Rosenblatt, et al., "Injectable collagen as a pH-senstitive hydrogel", Biomaterials, 1994, vol. 15, No. 12, pp. 985-995.

Ross, et al., "Association Between Peridural Scar and Recurrent Radicular Pain After Lumbar Discectomy: Magnetic Resonance Evaluation", Neurosurgery, 1996, vol. 38, No. 4, pp. 855-863.

Rossler, et al., "Collagen microparticals: preparation and properties", J. Microencapsulation, 1995, vol. 12, No. 1, pp. 49-57.

San-Galli, et al., "Experimental Evaluation of a Collagen-coated Vicryl Mesh as a Dural Substitute", Neurosurgery, 1992, pp. 396-401.

Shaffrey, et al., "Neurosurgical Applications of Fibrin Glue: Augmentation of Dural Closure in 134 Patients", Neurosurgery, 1990, pp. 207-210.

Smith, et al., "Delayed postoperative tethering of the cervical spinal cord", J. Neurosurg., 1994, vol. 81, pp. 196-201.

Springorum, "The Use of Collagen Films for Bridging over Defects of Gliding Tissue in Raptures of Achilles Tendon", Akt. Traumarol., 1985 (English Abstract).

Stricker, et al., "The application of TissuFoil membrane for sinusaugmentation", Ellipse, 2001 (English Abstract).

Sugitachi, et al., "A newly devised chemo-embolic agent", Gan To Kagaku Ryoho, 1985.

Sugitachi, et al., "Locoregional therapy in patients with malignant pleural effusion-two different types of BAC therapy", Gan To Kagaku Ryoho, 1992.

Sugitachi, et al., "Preoperative transcatheter arterial chemoembolization for locally advanced breast cancer. Application of new thrombotic materials", Japan J. surg., 1983.

Kofidis, et al., "Clinically Established Hemostatic Scaffold (Tissue Fleece) as Biomatrix in Tissue—and Organ-Engineering Research", Tissue Engineering, 2003, vol. 3, No. 9, pp. 517-524.

Baxter Package Leaflet—TissueFleece E, Ver. 5, English version of instructions for use, 2003.

Tobin, et al., "Pligged Liver Biopsy in Patients wit Impaired Coagulation", Digestive Disease and Science, 1989, vol. 34, No. 1, pp. 13-15.

Tucker, et al., "Absorbable Gelatin (Gelfoam) Sponge", 1965, pp. 1-125.

Vander Salm, et al., "Reduction of sternal infection by application of topical vancomycin", J. Thorac. Surg., 1989, vol. 98, pp. 618-622.

Vinas, et al., "Evaluation of expanded polytetrafluorethylene (ePTFE) versus polydioxanone (PDS) for the repair of dura mater defects", Neurological Research, 1999, vol. 21, pp. 262-268.

Wallace, et al., "Injectable cross-linked collagen with improved flow properties", J. Biomedical Materials Research, 1989, vol. 23, pp. 931-945.

Wallace, et al., "The Relative Contribution of Electrostatic Interactions to Stabilization of Collagen Fibrils", Biopolymers, 1990, vol. 29, pp. 1015-1026.

Warren, et al., "Dural Repair Using Acellular Human Dermis: Experience with 200 Cases: Technique Assesment", Neurosurgery, 2000, vol. 46, No. 6, pp. 1391-1396.

Yuki, et al., "Effects of endoscopic variceal sclerotherapy using GT XIII on blood coagulation tests and the renal kallikrein-kinin system", Gastroentral. Japan, 1990.

Ziegelaar, et al., "The characterisation of human respiratory epithelial cells cultured on resorbable scaffolds: first steps towards a tissue engineered tracheal replacement", Biomaterials, 2002, vol. 23, pp. 1425-1438.

Ziegelaar, "Tissue Engineering of a Tracheal Equivalent", Doctorial Thesis, 2004.

Zins, et al "US-guided Percutaneous Liver Biopsy with Plugging of the Needle Track: A Prospective Study in 72 High-Risk Patients", Radiology, 1992.

International Preliminary Report on Patentablility and Written Opinion for PCT/US2007074984, mailed Feb. 17, 2009.

Product Brochure for Gelfoam, Jul. 1, 1996.

Delustro, et al., "A comparative study of the biologic and immunologic response to medical devices derived from dermal collagen", Journal of Biomedical Materials Research, 1986, vol. 20, pp. 109-120.

Japanese Office Action for JP Appl. No. 2001-502866, mailed Dec. 28, 2009.

Coenye, et al., "A Qualitative Morphological Comparison of Two Haemostatic Agents in a Porcine Liver Trauma Model", Surgical Science, 2013, vol. 4, pp. 359-364.

Current Gelfoam Label, 2013.

Guinto, "Preparation of Gelfoam Particles Using an Orthopedic Rasp", 1984.

Lewis, et al., "Comparison of Two Gelatin and Thrombin Combination Hemostats in a Porcine Liver Abrasion Model", Journal of Investigative Surgery, 2013, vol. 26, pp. 141-148.

Harris, et al., "Topical Hemostatic Agents for Bone Bleeding in Humans", Journal of Bone and Joint Surgery, 1978, pp. 454-456.

Oz, et al., "Controlled Clinical Trial of a Novel Hemostatic Agent in Cardiac Surgery", Ann Thorac Surg, 2000, vol. 69, pp. 1376-1382.

Schramm, Jr., et al., "Gelfoam Paste Injection for Vocal Cord Paralysis: Temporary Rehabilitation of Glottic Incompetence", The Laryngoscope, 1978, pp. 1268-1273.

Millikan, et al., "Treatment of depressed cutaneous scars with gelatin matrix implant: A Multicenter study", Journal of the American Academy of Dermatology, 1987, pp. 1155-1162.

Boyers, et al., "Reduction of postoperative pelvic adhesions in the rabbit with Gore-Tex surgical membrane", Fertility and Sterility, vol. 49, No. 6, 1988, pp. 1066-1070.

Heller, et al., "Release of Norethindrone from Poly(Ortho Esters)", Polymer Engineering Science, vol. 21, No. 11, 1981, pp. 727-731.

(56) References Cited

OTHER PUBLICATIONS

Jeong, et al., "Biodegradeable block copolymers as injectable drug-delivery systems", Nature, 1997, vol. 388, pp. 860-862.
Langer, et al., "Chemical and Physical Structure of Polymers as Carriers for Controlled Release of Bioactive Agents: A Review", Rev. Macromol. Chem. Phys., pp. 61-128, 1983.
Leong, et al., "Polymeric controlled drug delivery", Advanced Drug Delivery Reviews, 1987, pp. 199-233.
Leong, et al., "Polyanhydrides for controlled release of bioactive agents", Biomaterials, 1986, pp. 364-371.
Masar, et al., "Synthesis of Polyurethanes and Investigation of Their Hydrolytic Stability", Journal of Polymer Science: Polymer Symposium, 1979, vol. 66, pp. 259-268.
Sidman, et al., "Biodegradeable, Implantable Sustained Release Systems Based on Glutamic Acid Copolymers", Journal of Membrane Science, 1980, vol. 7, pp. 277-291.
Gibble, et al., "Fibrin Glue: The perfect operative sealant?", Transfusion, 1990, vol. 30, No. 8, pp. 741-747.
Ansell, et al., "Gelfoam and Autologous Clot Embolization: Effect on Coagulation", Investigative Radiology, 1978, vol. 13, pp. 115-120.
Barrow, et al., "The use of greater omentum vascularized free flaps for neurosurgical disorders requiring reconstruction", J. Neurosug., 1984, vol. 60, pp. 304-311.
Barton, et al., "Fibrin glue as a biologic vascular patch-a comparative study", J. Surg. Res., 1986, vol. 40 (5), pp. 510-513.
Baxter product brochure for TissuFleece E, Version 5, 2003.
Baxter Product Catalogue: Collagen, 2006.
Bruck, "Controlled Drug Delivery", 1983.
Cantor, et al., "Gelfoam and Thrombin in Treatment of Massive Gastroduodental Hemorrhage", Am. J. Surg., 1950, pp. 883-887.
Cantor, et al., "Gelfoam and Thrombin in Treatment of Massive Upper Gastroduodental Hemorrhage", Am. J. Surg., 1951, pp. 230-235.
Cantor, et al., The Journal of Laboratory and Clinical Medicine, 1950, vol. 35, pp. 890-893.
Chaplin, et al., "Use of an Acellular Dermal Allograft for Dural Replacement: An Experimental Study", Neurosurgery, 1999, vol. 45, No. 2, pp. 320-327.
Cheung, et al., "Mechanism of Crosslinking of Proteins by Glutaraldehyde IV: In Vitro and in Vivo Stability of a Crosslinked Collagen Matrix", Connective Tissue Research, 1990, vol. 25, pp. 27-34.
Christensen, et al., Drug Development and Industrial Pharmacy, 1997, vol. 23, No. 5, pp. 451-463.
Chuang, et al., "Sheeth Needle for Liver Biopsy in High-Risk Patients", Radiology, 1988.
Collins, D., et al., "Enemata of Gelfoam Milk Suspension Combined with Thrombin-Solution to Control Massive Hemorrhage Following Anorectal Surgery", Am. J. Proctol., 1951, vol. 2, No. 2, pp. 60-63.
Collins, R., et al., "Use of collagen film as a dural substitute: Preliminary animal studies", Journal of Biomedical Materials Research, 1991, vol. 25, pp. 267-276.
Edgerton, et al., "Vascular Hamartomas and Hemangiomas: Classification and Treatment", Southern Med. J., 1982, vol. 75, No. 12, pp. 1541-1547.
Filippi, et al., Bovine pericardium for duraplasty: clinical results in 32 patients, Neurosurg Rev, 2001, vol. 24, pp. 103-107.
Baxter, "Biomaterials based on native-structure fibrillar collagen: The TissuFleece E collagen fleece product line", TissuFleece E Collagen Fleece, TissuCone E Collagen Cone, TissuFoil E Collagen Foil, Basic Scientific Information, 1999.
Hieb, et al., "Spontaneous Postoperative Cerebrospinal Fluid Leaks Following Application of Anti-Adhesion Barrier Gel", Spine vol. 26, No. 7, 2001, pp. 748-751.
Hood, et al., "Efficacy of Topical Hemostat Floseal Matrix in Vascular Surgery", 24th World Congress of the Int. Soc. of Cardiovascular Surg., 1999.
Hotz, et al., "Collagen and fibrin as biologic binders for granular hydroxylapatite", Dtsch Z Mund Kiefer Gesichtschir, 1989.
Jonas, R., et al., "A new sealant for knitted Dacron prostheses: Minimally cross-linked gelatin", J. Vasc. Surg., 1988, pp. 414-419.
Kim, et al., "Reduction in leg pain and lower-extremity weakness with Oxiplex/SP Gel for 1 year after laminectomy, laminotomy, and discectomy", Neurosurg. Focus, vol. 17, 2004, pp. 1-6.
Kline, "Dural Replacement with Resorbable Collagen", Arch. Surg., 1965, vol. 91, pp. 925-928.
Knopp, 12th European Congress of Neurosurgery (EANS), 2003, pp. 664-666.
Krill, et al., "Topical Thrombin and Powdered Gelfoam an Efficient Hemostatic Treatment for Surgery", J. Tenn. Dent. Assoc., 1986, vol. 66 (2), pp. 26-27.
Kuhn, et al., "Bilateral subdural haematomata and lumbar pseudomeningocele due to a chronic leakage if liquor cerebrospinalis after a lumbar discectomy with the application of ADCON-L gel", J. Neurol. Neurosurg. Psychiatry, 2005, pp. 1031-1033.
Laquerriere, et al., "Experimental evaluation of bilayered human collagen as a dural substitute", J. Neurosurg, 1993, vol. 78, pp. 487-491.
Larson, "Topical Hemostatic Agents for Dermatologic Surgery", J. Dermatol. Surg. Oncol., 1988, pp. 623-632.
Le, A., et al., "Unrecognized Durotomy After Lumbar Discectomy", Spine, 2001, vol. 26, No. 1, pp. 115-118.
Lee, J.F., et al., "Experimental Evaluation of Silicone-Coated Dacron and Collagen Fabric-Film Laminate as Dural Substitutes", J. Neurosurg., 1967, vol. 27, pp. 558-564.
Moak, "Hemostatic Agents: Adjuncts to Control Bleeding", Today's OR Nurse, 1991, pp. 6-10.
Matsumoto, et al., "A Gelatin Coated Collagen-Polyglycolic Acid Composite Membrane as a Dural Substitute", ASAIO Journal, 2001, pp. 641-645.
Maurer, et al., "Vicryl (polyglactin 910) mesh as a dural substitute", J. Neurosurg., 1985, vol. 63, pp. 448-452.
McClure, et al., "Massive Gastroduodental Hemorrhage: Treatment with Powdered, Gelfoam and Buffered Thrombin Solution", Surg., 1952, vol. 12, No. 4, pp. 630-637.
McPherson, J.M., et al., "An examination of the biologic response to injectable, glutaraldehyde cross-linked collagen implants", J. Biomed. Mater Res., 1986, vol. 20, pp. 93-107.
McPherson, J.M., et al., "The preparation and physicochemical characterization of an injectable form of reconstituted, glutaraldehyde cross-linked, bovine corium collagen", J. Biomed. Mater Res., 1986, vol. 20, pp. 79-92.
McPherson, J.M., et al., "The Effects of Heparin on the Physicochemical Properties of Reconstituted Collagen", Collagen Rel. Res., 1988, vol. 1, pp. 65-82.
Meddings, et al., "Collagen Vicryl—A New Dural Prosthesis", Acta Neurochir., 1992, vol. 117, pp. 53-58.
Mello, et al., "Duroplasty with biosynthetic cellulose: An experimental study", J. Neurosurg., 1997, vol. 86, pp. 143-150.

* cited by examiner

HEMOSTATIC COMPOSITIONS CONTAINING STERILE THROMBIN

CROSS REFERENCE TO RELATED APPLICATIONS

This application is a continuation of U.S. application Ser. No. 10/567,388, now U.S. Pat. No. 7,718,412, filed Feb. 7, 2006, which is a National Stage application under 35 U.S.C. 371 of PCT/US2004/023765, filed Jul. 23, 2004, which claims priority from U.S. Provisional Application Ser. No. 60/493,116, filed Aug. 7, 2003. The benefit of U.S. application Ser. No. 10/896,647, filed on Jul. 22, 2004, is also claimed, now abandoned.

FIELD

The present invention relates to hemostatic compositions containing sterile thrombin and to methods of making such hemostatic compositions.

BACKGROUND

Gelatin-based hemostats, both in solid sponge or powder form, are commercially available and are used in surgical procedures. Gelatin powder, when mixed with fluid, can be prepared in various forms depending on the contemplated end-use and the ratio of fluid to powder. For example, where higher concentrations of fluid are employed, a paste or slurry that is useful as a flowable, extrudable and injectable hemostat may be prepared for use in diffuse bleeding, particularly from uneven surfaces or hard to reach areas. Such conventional slurries are prepared at the point of use by mechanical agitation and mixing of the powder and liquid to provide uniformity of the composition. The paste then is placed into a delivery means or applicator, e.g. a syringe, and applied to the wound. In other cases, moldable compositions may be prepared with lower amounts of fluid and molded or packed to form a dressing for use on external wounds. Gelatin powders are sterilized prior to preparing such compositions but mixing of the powders and fluids may compromise the sterility of the hemostatic composition due to handling of the materials at the site of use, or in general by exposure to the environment for relatively extended periods of time during mixing and the like.

Thrombin that is not terminally sterilized is known to be used in combination with such hemostatic compositions. Proteins such as thrombin are prepared aseptically and thus there is a risk that nonsterilized proteins such as thrombin, when used in hemostatic compositions, may compromise the sterility of the previously-sterilized materials, such as sterilized gelatin powder. However, as thrombin is known to be denatured by exposure to sterilizing condition such as ionizing radiation conventionally used to sterilize the powders, which denaturing destroys all enzymatic activity of the thrombin, thrombin has not been reported to be incorporated into the hemostatic compositions and then terminally sterilized prior to use to ensure a sterile composition. In fact, when thrombin is used in conventional hemostatic compositions, nonsterilized thrombin is added after sterilization of hemostatic composition.

It would be desirable if a sterile hemostatic composition containing active sterile thrombin was available to the surgeon at the point of use without need for preparation, e.g. without having to add thrombin prior to use. The compositions of the present invention fulfill that need.

SUMMARY

The present invention is directed to sterilized hemostatic compositions comprising a continuous, biocompatible liquid phase, a solid phase comprising porous or non-porous particles of a biocompatible polymer suitable for use in hemostasis and which are substantially insoluble in the liquid phase, and sterile thrombin. The continuous liquid phase comprises the solid particulate phase and sterile thrombin substantially homogeneously dispersed there through. The ratio of the liquid phase, the solid particulate phase and thrombin is effective to provide the composition with hemostatic properties, both prior to and after sterilization. Sterile compositions of the present invention may be prepared well in advance of the time of use while maintaining thrombin enzymatic activity even after being subjected to sterilizing radiation. The present invention also includes methods of making the hemostatic compositions.

DETAILED DESCRIPTION

Sterilized compositions of the present invention contain solid, porous or non-porous particles of a biocompatible polymer suitable for use in hemostasis, a biocompatible liquid and sterile thrombin as its three primary components. Particles, liquid and thrombin are combined and mixed under conditions effective to provide a substantially homogeneous hemostatic composition comprising a continuous liquid phase comprising the thrombin and having the solid polymer particles homogeneously dispersed there through. The amount and average diameter of particles contained in the composition and the relative amounts of the solid, liquid and thrombin is effective to provide the composition with hemostatic and physical properties, as described herein below.

Compositions of the present invention may be prepared and sterilized by ionizing irradiation well in advance of the time of their intended use, while maintaining thrombin enzymatic activity effective to improve hemostasis of the composition when compared to a similar composition containing no thrombin or where the thrombin activity has been substantially diminished such that it no longer enhances hemostasis. This is particularly surprising given that it is known in the art that thrombin is denatured when exposed to irradiation of the type used to sterilize conventional hemostatic compositions containing, for example, gelatin powder. Denaturing causes the thrombin to lose its enzymatic activity. The compositions further may include additives to facilitate the preparation of the composition, enhance physical and mechanical properties, enhance the hemostatic properties of the composition or provide antimicrobial properties.

As used herein, "continuous" and "discontinuous" are used in the ordinary meaning of those words in the context of standard nomenclature used to define and describe dispersions.

As used herein, "substantially homogeneous" denotes that physical state of the compositions or pastes where the solid particles are uniformly dispersed throughout the continuous liquid phase such that the ratio of solid:liquid and the density of any portion or cross-section of the composition or paste are substantially the same.

As used herein, "sterile" means substantially free of living germs and/or microorganisms and as further recognized and described by governmental standards pertaining to compositions and medical devices described and claimed herein.

As used herein, "hemostatic", or "hemostatic properties", means the ability to stop or minimize bleeding, as one skilled in the art of hemostasis would understand those terms to mean, as further exemplified in the examples of the specification.

A variety of biocompatible natural, semi-synthetic or synthetic polymers may be used to prepare the solid particles used in compositions of the present invention. The polymer selected must be substantially insoluble in the liquid chosen for the particular composition. Preferably, water-insoluble biodegradable polymers that provide mechanical, chemical and/or biological hemostatic activity are used. Polymers that may be used include, without limitation, proteins and polysaccharides. Polysaccharides that may be used include oxidized cellulose, chitosan, chitin, alginate, oxidized alginate and oxidized starch. The biocompatible polymer used to prepare the particles preferably is a cross-linked or denatured protein, such as gelatin, collagen, fibrinogen or fibronectin. A preferred gelatin powder is a partially cross-linked gelatin powder prepared by milling gelatin sponge into particles having an average diameter of from about 40 microns to about 1200 microns, more preferably from about 100 microns to about 1000 microns, as determined by laser diffraction.

Sterile compositions of the present invention comprise a continuous liquid phase in which the sterile thrombin and solid particles are dispersed. Depending upon the particular medical device and use thereof, the liquid may be aqueous or non aqueous. Preferably, the liquid phase is aqueous. Aqueous liquids may include, without limitation, biocompatible aqueous solutions, such as calcium chloride and saline. More preferably, the liquid phase comprises saline. The liquid phase and solid particulate phase are present in relative amounts effective to provide a composition, for example a paste, or slurry, suitable for use in providing hemostasis. In certain embodiments, the weight ratio of solid particles to liquid generally is from about 1:1 to about 1:12, or from about 1:3 to about 1:8 or even about 1:5.

Compositions of the present invention include compositions described herein that are sterile, in that they have been irradiated with a level of, e.g. ionizing irradiation. Such irradiation may include e-beam or gamma irradiation. The level of irradiation and conditions of sterilization, including the time that the compositions are irradiated, are those that provide sterile compositions, as defined herein. Once having the benefit of this disclosure, one skilled in the art will be able to readily determine the level of irradiation necessary to provide sterile compositions.

As noted herein, thrombin, in an aqueous solution, has been found to lose all procoagulant activity when exposed to sterilization irradiation. In contrast, sterile thrombin contained in compositions of the present invention retain enzymatic activity sufficient to provide hemostatic properties to compositions of the present invention after being subjected to irradiation sufficient to provide sterilized compositions disclosed herein. Sterile thrombin in compositions of the present invention may lose only about 20 percent of its original enzymatic activity prior to sterilization. In certain embodiments of the present invention, the sterile thrombin exhibited a loss of enzymatic activity of not more than about 40% of its original enzymatic activity prior to sterilization, while maintaining all of its hemostatic activity after sterilization, when formulated in compositions according to this invention. While bovine thrombin is exemplified herein, human-derived thrombin, as described in U.S. Pat. No. 5,143,838, also may be used in compositions of the present invention. The discovery that thrombin will maintain activity after being exposed to sterilizing radiation as described above is particularly surprising given the previous teachings of the art that would strongly suggest that if thrombin were to be used in hemostatic compositions it should be added after sterilization of the composition, not prior to sterilization.

The hemostatic compositions may further comprise effective amounts of one or more additives or compounds including, but not limited to, antimicrobial agents, surfactants, antioxidants, humectants, wetting agents, lubricants, thickeners, diluents, irradiation stabilizers, e.g. radical scavengers, plasticizers, and stabilizers. For example, glycerol may be added to enhance the extrudability or injectability of the composition. When utilized, glycerol may be present in the compositions at from about 0% to about 20% by weight, based on the weight of the liquid phase. Preferably, the composition may comprise from about 1% to about 10% by weight of glycerol, based on the weight of the liquid phase. More preferably, the compositions may comprise from about 1% to about 5% by weight of glycerol, based on the weight of the liquid phase.

In addition, quaternary amines may be used to provide enhanced properties to the compositions. For example, benzalkonium chloride, Polybrene or Onamer M may be used at levels up to about 1 percent by weight, based on the weight of the liquid phase. Preferably, benzalkonium chloride is used at levels of from about 0.001% to about 0.01% by weight, based on the weight of the liquid phase. More preferably, the compositions may comprise from about 0.002 to about 0.006% by weight benzalkonium chloride, based on the weight of the liquid phase. It is believed that the quaternary amines may serve multiple functions, acting as an antimicrobial agent, a foaming agent, a radical scavenger and as a heparin neutralizer.

Such hemostatic compositions may further comprise heparin neutralizers, additional procoagulants or hemostatic agents, such as fibrinogen, fibrin, Factor Xa, or Factor VIla. By "effective amount", it is meant that amount necessary to provide to the compositions those properties for which the additive is being added. The effective amount also is limited by the maximum amount that may be added without causing detrimental biological affects.

Medical devices in which the hemostatic compositions of the present invention may be utilized include any device currently being used to apply a flowable or injectable hemostatic paste or slurry to a site, or wound, requiring hemostasis. The site requiring hemostasis may be the result of an injury or a surgical procedure. Examples of devices or applicators include syringes such as Becton Dickinson or Monoject luer syringes. Other devices are disclosed in detail in U.S. Pat. No. 6,045,570, the contents of which are incorporated by reference in their entirety.

In one embodiment for making compositions of the invention, a substantially homogeneous paste is prepared by mixing the particles with the liquid to form a uniform paste. The liquid includes the thrombin and may include effective amounts of other additives dissolved therein as described above. Mixing may be accomplished by extrusion or by mixing in a confined space under conditions effective to provide a uniform dispersion of the solid particles in the liquid phase.

Alternately, a mixer, e.g. a double planetary mixer, may be utilized in making compositions of the present invention. The liquid containing the thrombin is added to the mixer. The liquid may include effective amounts of additives dissolved therein prior to addition of particles to the solution. For example, a saline solution containing thrombin, glycerol and benzalkonium chloride may be prepared and then added to the mixer. The solid particles are added to the mixer over time with continuous mixing until all ingredients have been added. The mixing is continued until such time as a substantially homogenous composition is formed containing the solid particles uniformly dispersed throughout the continuous liquid phase.

The hemostatic compositions prepared as above are sterilized to provide sterile compositions comprising sterile thrombin. In some embodiments the compositions are transferred into a medical device as described above and the device containing the hemostatic composition is sterilized, preferably by ionizing radiation. More preferably, sterilization is by gamma irradiation as exemplified herein.

While the following examples demonstrate certain embodiments of the invention, they are not to be interpreted as limiting the scope of the invention, but rather as contributing to a complete description of the invention.

Example 1

Two vials of lyophilized Bovine thrombin (20,000 units Thrombogen JJMI) were reconstituted in 20 ml of saline to provide a working solution of 1,000 units/ml. Clotting activity was measured in an in vitro test as described in Example 2. One vial of this material was stored at 4-8° C. and the clotting activity measured at day 1, day 8 and day 30, respectively. The second vial was sterilized by gamma irradiation (25 kGy) and the clotting activity measured as above. The unsterilized and sterilized samples were designated samples 1a and 1b, respectively. Both sterilized and unsterilized samples were stored at 4-8° C. between measurements.

Another 2 vials of 20,000 units of lyophilized bovine thrombin were reconstituted in saline containing 0.005% benzalkonium chloride and 5% glycerol. One vial was stored at. 4-8° C. and the clotting activity was measured at day 0, day 1, day 8 and day 30. The second vial was sterilized by gamma irradiation (25 kGy) and the clotting activity measured as above. In between measurements both the sterilized and unsterilized samples were stored at 4-8° C. The unsterilized and sterilized samples were designated samples 1c and 1d, respectively.

Several samples of gelatin paste containing the thrombin noted above were prepared by mixing 1 gram of Surgifoam gelatin powder with 5 ml of thrombin solution. The resulting paste was loaded into a 10 cc syringe. Samples were then either sterilized at 25 kGy followed by storage at 4-8° C., or stored unsterilized at 4-8° C. Samples so prepared are designated and identified below.

Sample 1e=1 g Surgifoam® powder plus 5 ml of sample 1a; Sterilized

Sample 1f=1 g Surgifoam® powder plus 5 ml of sample 1c; Unsterilized

Sample 1 g=1 g Surgifoam® powder plus 5 ml of sample 1c; Sterilized.

Example 2

Measurement of Thrombin activity by an in vitro coagulation test in a Fibrometer instrument (BBL).

Method: Serial dilutions of test sample containing thrombin were prepared in Veronal buffer pH 7.2. 0.2 ml of pooled normal plasma (Citrol Level I control plasma-Dade Diagnostics) was warmed to 37° C. in the fibrometer incubator block. 0.1 ml of pre-warmed sample dilution was added to the plasma and the timer started simultaneously. The time to clot formation was recorded. All samples were tested in duplicate and an average clotting time calculated. Data was graphed as the $\log_{10}$ dilution vs. login clotting time and a regression analysis performed. Freshly prepared thrombin was considered to have 100% activity and all other samples were calculated as a percentage of the activity relative to the freshly prepared thrombin. Results are presented in Table 1 and Table 2.

TABLE 1

Effect of Storage time on Thrombin Activity: Stabilization by Formulated Gelatin Paste

| Storage Solution | Percent Loss in Thrombin Activity | | | |
|---|---|---|---|---|
| (Stored at 6° C.) | Time 0 | Day 1 | Day 8 | Day 30 |
| 1a | 0 | 0 | 53.3 | 90.8 |
| 1c | 0 | NA | 41.1 | 82.9 |
| 1f | 0 | 0 | 0.8 | 0 |

TABLE 2

Effect of Gamma Irradiation on Thrombin Activity: Stabilization by Formulated Gelatin Paste

| Media for Sterilized Thrombin * Samples (Smug gelatin powder- 25 kGy Dose) | % Loss in Thrombin Activity Day 6 |
|---|---|
| 1b | 100 |
| 1d | 96.0 |
| 1e | 72.6 |
| 1g | 79.2 |

TABLE 3

In vivo Hemostasis Performance of Pre-filled Thrombin/Gelatin Paste

| TIME: SAMPLE | Number of Compressions | Time to Hemostasis (mins:secs) |
|---|---|---|
| Day 0: 1f | 1 | 0:30 |
| Day 42: 1f | 1 | 0:30 |
| Day 42: 1f | 1 | 0:30 |
| Day 42: 1g | 1 | 0:30 |
| Day 42: 1g | 1 | 0:30 |

Example 3

Sterilization of Frozen Thrombin by Gelatin Paste

One vial of 20,000 units of lyophilized bovine thrombin (Thrombogen JJMI) was reconstituted in saline containing 0.005% BAK and 5% glycerol. 1 gram of Surgifoam® powder was mixed with 5 ml of thrombin-containing saline solution. The resulting paste was loaded into a 10 ml syringe. The sample were frozen at −20° C. and sterilized by gamma irradiation at a dose of 25 kG. Thrombin clotting activity was measures as described in Example 2. It was noted that only 42 percent of thrombin activity was lost due to sterilization.

While the present inventions have been described in connection with a number of exemplary forms, and implementations, the present inventions are not so limited, but rather cover various modifications, and equivalent arrangements, which fall within the purview of the present claims.

What is claimed:

1. A sterile hemostatic composition, comprising:
   a continuous, biocompatible liquid phase comprising sterile thrombin having enzymatic activity; and
   a solid phase comprising particles of a biocompatible polymer suitable for use in hemostasis and which is substantially insoluble in said liquid phase, said continuous liquid phase comprising said solid phase and said sterile thrombin substantially homogeneously dispersed there-through, wherein the ratio of said liquid phase and said solid phase is effective to provide said composition with hemostatic properties and wherein said sterile thrombin has lost not more than about 40 percent of the enzymatic activity possessed prior to sterilization.

2. The sterile hemostatic composition of claim 1 wherein said liquid phase comprises saline.

3. The sterile hemostatic composition of claim 2 wherein said biocompatible polymer is selected from the group consisting of proteins and polysaccharides.

4. The sterile hemostatic composition of claim 3 wherein said protein is selected from the group consisting of gelatin, collagen, fibrinogen and fibronectin.

5. The sterile hemostatic composition of claim 4 wherein said protein is gelatin.

6. The sterile hemostatic composition of claim 1 wherein said sterile thrombin has lost not more than about 20 percent of the enzymatic activity it possessed prior to sterilization.

* * * * *